US009568412B2

(12) United States Patent
Kajiyama

(10) Patent No.: US 9,568,412 B2
(45) Date of Patent: Feb. 14, 2017

(54) METHOD AND INSTRUMENTATION FOR MEASURING AND ASSESSING AC CORROSION RISK OF PIPELINE

(75) Inventor: Fumio Kajiyama, Tokyo (JP)

(73) Assignee: TOKYO GAS CO., LTD., Tokyo (JP)

( * ) Notice: Subject to any disclaimer, the term of this patent is extended or adjusted under 35 U.S.C. 154(b) by 251 days.

(21) Appl. No.: 14/240,944

(22) PCT Filed: Jun. 4, 2012

(86) PCT No.: PCT/JP2012/064379
§ 371 (c)(1),
(2), (4) Date: Feb. 25, 2014

(87) PCT Pub. No.: WO2013/080587
PCT Pub. Date: Jun. 6, 2013

(65) Prior Publication Data
US 2014/0225631 A1 Aug. 14, 2014

(30) Foreign Application Priority Data
Nov. 29, 2011 (JP) .................. 2011-260861

(51) Int. Cl.
G01N 17/02 (2006.01)
G01N 17/04 (2006.01)
(52) U.S. Cl.
CPC ............ G01N 17/043 (2013.01); G01N 17/02 (2013.01)
(58) Field of Classification Search
CPC .............................. G01N 17/02; G01N 17/043
See application file for complete search history.

(56) References Cited

U.S. PATENT DOCUMENTS

| 5,216,370 A | 6/1993 | Bushman et al. |
| 2008/0036476 A1* | 2/2008 | Nielsen .................. G01N 17/02 324/700 |
| 2011/0238347 A1* | 9/2011 | Gemperli ................ C23F 13/04 702/65 |

FOREIGN PATENT DOCUMENTS

| JP | 06-288897 | 10/1994 |
| JP | 2002-296213 | 10/2002 |

(Continued)

OTHER PUBLICATIONS

Extended European Search Report (EESR) from European Patent Office (EPO) in European Patent Application No. 12853255.3, dated Jun. 10, 2015.

(Continued)

Primary Examiner — Tung X Nguyen
Assistant Examiner — Feba Pothen
(74) Attorney, Agent, or Firm — Greenblum & Bernstein, P.L.C.

(57) ABSTRACT

A measuring and assessing method for the AC corrosion risk of a pipeline wherein the coupon is connected to a metallic pipeline buried in the earth and the AC corrosion risk of the pipeline is assessed on the basis of coupon DC current density and coupon AC current density that are acquired from a measured value of a coupon current, wherein the measuring and assessing method includes: a step of specifying frequency to specify a source of AC corrosion from a waveform of the measured value of the coupon current; and a step of calculating a coupon current density whereby a pair of coupon DC current density and coupon AC current density is acquired from the measured value of the coupon current in one time unit by defining one cycle of a specified frequency as one time unit.

11 Claims, 5 Drawing Sheets

(56) References Cited

FOREIGN PATENT DOCUMENTS

| JP | 2007-191733 | 8/2007 |
|----|-------------|--------|
| JP | 2008-281433 | 11/2008 |
| JP | 2009-156707 | 7/2009 |
| JP | 2011-191288 | 9/2011 |

OTHER PUBLICATIONS

International Search Report (ISR) in International Patent Application No. PCT/JP2012/064379, dated Sep. 11, 2012.
W. V. Baeckmann et al., "Handbuch des kathodischen Korrosionsschutzes," WILEY-VCH Verlag GmbH, Weinheim, Deutschland, 1999, p. 516.
"Handbook Of Stray Current Control and Cathodic Protection," edited by the Electrolytic Corrosion Prevention Research Committee of the Instutue of Electrical Engineers of Japan (IEEJ), Ohmsha, Ltd., Jan. 20, 2011, pp. 126-129.
Office Action from Europoean Patent Office (EPO) in European Pat. Appl. No. 12853255.3, dated Feb. 17, 2016.
Office Action from European Patent Office (EPO) in European Patent Appl. No. 12853255.3, dated Oct. 28, 2016.

\* cited by examiner (a)

(a)

METHOD AND INSTRUMENTATION FOR MEASURING AND ASSESSING AC CORROSION RISK OF PIPELINE

FIELD OF THE INVENTION

The present invention relates to a method and instrumentation for measuring and assessing the AC corrosion risk of a pipeline by measuring a coupon current.

BACKGROUND OF THE INVENTION

In recent years, metallic pipelines buried in the earth (hereinafter, simply referred to as pipeline(s)) whose external surface is covered with plastic coatings having high resistivity and pipelines are being increasingly laid over long distances in parallel with high voltage AC electric power lines and/or AC powered rail transit systems, and therefore a need for measuring and assessing the AC corrosion risk of pipelines is increasing. According to analysis results of AC corrosion incidents of pipelines, it can be said that a source of AC corrosion is high voltage AC electric power lines or AC powered rail transit systems which run in parallel with the pipelines. AC corrosion occurs at a coating defect of pipelines while AC voltage is induced on the pipelines affected by these sources of AC corrosion. As such, AC current density $I_{AC}$ [A/m²] in the area of a coating defect is an index for obtaining AC corrosion rate.

AC current density $I_{AC}$ [A/m²] in the area S of a coating defect is defined as $I_{AC}=V_{AC}/(R*S)$, (where, $V_{AC}$: induced AC voltage on a pipeline, R: resistance to earth of a coating defect). Assuming a coating defect is circular shaped with diameter of d [m], resistance to earth of a coating defect R [Ω] is represented by R=ρ/(2d) (where, ρ: electrolyte resistivity [Ω*m]; see non-patent literature 1 shown below). Thus, the AC current density $I_{AC}$ [A/m²] in the area S [m²] at the coating defect can be represented by the following equation.

$$I_{AC}=2.26j*\omega*M*I*L/[\rho*(S^{1/2})]$$

Where,
j: imaginary unit,
ω: 2πf (f: frequency of a current flowing through an electric power line or a trolley line)
M: mutual inductance between an electric power line or a trolley wire and a buried coating pipeline
I: current of an electric power line or current of a trolley wire
L: parallel-running distance between an electric power line or a trolley wire and a buried coating pipeline As is apparent from the equation, the greater the induced AC voltage $V_{AC}$ (that is, the greater the current flow of the high voltage AC electric power lines or the greater the current flow of the trolley wires of the AC powered rail transit systems, and/or the longer the parallel running distance between the electric power lines or the trolley lines and the pipelines), the lower the resistivity ρ of the electrolyte in contact with the coating defect, and the smaller the area S of the coating defect, the larger the AC current density $I_{AC}$ increases, and thus the higher AC corrosion rate increases. Further, from another point of view, even if the AC voltage $V_{AC}$ is not that large, when the resistivity ρ of the electrolyte in contact with the coating defect is low and the area S of the coating defect is small, the AC current density $I_{AC}$ increases, and thus AC corrosion rate increases.

The AC current density of the coating defect in the coated pipelines buried in the earth cannot be actually measured. As such, the AC corrosion risk of pipelines is assessed by electrically connecting the coupon which is buried in the proximity of the pipelines with the pipelines and comparing two values of coupon DC current density and coupon AC current density (collectively these two values are called coupon current density) which are acquired from a measured value of current flowing through the connected wire with a cathodic protection reference which employs the coupon current density as an index. Where, the coupon simulates the coating defect of the pipelines and is a metal piece that is made of the same metal material as the pipelines having a known surface area (see below-mentioned non-patent literature 2).

RELATED ART

Non-Patent Literature

[Non-patent literature 1] W. V. Baeckmann and W. Schwenk: Handbuch des kathodischen Korrosionsschutzes, WILEY-VCH Verlag GmbH, Weinheim, Deutschland, 1999

[Non-patent literature 2] "Handbook of Stray Current Control and Cathodic Protection" edited by the Electrolytic Corrosion Prevention Research Committee of the Institute of Electrical Engineers of Japan (IEEJ). Ohmsha, Ltd. Jan. 20, 2011. Page 123 to 156.

SUMMARY OF THE INVENTION

Problems to be Solved by the Invention

FIG. 1 is a view illustrating a method for measuring coupon current density on a pipeline. As shown in FIG. 1(a), the coupon C is buried in the earth in the proximity of a pipeline P and the coupon C and the pipeline P are electrically connected with a wire W. The external surface of the pipeline P is covered with a coating P1 made of a plastic material and the surface area A at the tip C1 of the coupon C simulates the defect of the coating P1. A shunt resistor Rs is provided in the wire W which electrically connects the coupon C with the pipeline P. Coupon DC current density $I_{DC}$ and coupon AC current density $I_{AC}$ are measured by measuring instrumentation M that measures current (coupon current) flowing through the shunt resistor Rs.

According to an example shown in FIG. 1(b), coupon DC current density $I_{DC}$ and coupon AC current density $I_{AC}$ can be acquired from measured values (I(1), I(2), I(3), . . . ) of coupon current that is sampled at intervals of 0.1 ms. An AC cycle of the source of AC corrosion (for example, a high voltage AC electric power lines and/or an AC powered rail transit systems) is set to be one subunit, and the coupon DC current density $I_{DC}$ and the coupon AC current density $I_{AC}$ are defined to be acquired for each subunit as a pair of coupon DC current density $I_{DC}$ and coupon AC current density $I_{AC}$ and the average value $I_{DC}^{ave}$, the maximum value $I_{DC}^{max}$ and the minimum value $I_{DC}^{min}$ of the coupon DC current density $I_{DC}$, and the average value $I_{AC}^{ave}$, the maximum value $I_{AC}^{max}$ and the minimum value $I_{AC}^{min}$ of the coupon AC current density $I_{AC}$ are acquired for each unit constituted by a plurality of subunits.

An example shown in FIG. 1(b) has commercial frequency of 50 Hz (cycle of 20 ms) for the source of AC corrosion. In this case, a single subunit is set as 20 ms and 200 measured values (I(1), I(2), I(3), . . . I(199), I(200)) are sampled during the single subunit. From the measured values I(t)(t=1 to 200) the coupon DC current density $I_{DC}$ and the coupon AC current density $I_{AC}$ are acquired on the basis of the following equations (1) and (2) (Where, A represents the surface area of the coupon).

$$I_{DC} = \frac{1}{A} \frac{1}{200} \sum_{t=1}^{200} I(t) \quad (1)$$

$$I_{AC} = \frac{1}{A} \sqrt{\frac{1}{200} \sum_{t=1}^{200} \{I(t) - I_{DC}\}^2} \quad (2)$$

When acquiring the coupon DC current density $I_{DC}$ and the coupon AC current density $I_{AC}$ which are defined by the aforementioned equation, it is assumed that the commercial frequency for the source of AC corrosion is preliminarily determined, and each subunit is delimited by one cycle of the commercial frequency so that the pair of the coupon DC current density $I_{DC}$ and the coupon AC current density $I_{AC}$ are acquired. However, there are three commercial frequencies that are 16⅔ Hz, 50 Hz and 60 Hz for the source of AC corrosion and different frequencies are employed for each region and for each usage. For example, in France, the frequencies for high voltage AC electric power lines and AC electric powered rail transit systems are same 50 Hz, while in Germany, the frequency for high voltage AC electric power lines is 50 Hz but the frequency for AC electric powered rail transit systems is 60 Hz. In Japan, the frequency for high voltage AC electric power lines is 50 Hz in eastern Japan and 60 Hz in western Japan. However since Tokaido Shinkansen is operated at 60 Hz from Tokyo, both 50 Hz and 60 Hz can be the frequency for the source of AC corrosion in Kanto region.

On the other hand, the coupon DC current density $I_{DC}$ and the coupon AC current density $I_{AC}$ are conventionally measured on the basis of a fixed subunit intended for a single commercial frequency, and thus there has been a problem that a measuring and assessing instrumentation cannot be used jointly across regions where different commercial frequencies are employed. Additionally, if the coupon AC current density $I_{AC}$ is acquired with respect to a commercial frequency with a cycle that is different from a measuring time of the fixed subunit by using the measuring and assessing instrumentation of the fixed subunit, an accurate coupon AC current density $I_{AC}$ that is suitable for assessing the AC corrosion risk cannot be acquired.

Further, there are cases where the source of AC corrosion cannot be clearly specified or mixed effects are brought by the source of AC corrosion that used different commercial frequencies at a measuring point for the coupon current density, and thus the measuring time of the subunit for acquiring the coupon current density may not be set when acquiring the coupon current density. In this case, when the measuring time of the fixed subunit that was preliminarily set is different from the AC cycle of the source of AC corrosion that has effect on the pipelines, the accurate coupon AC current density $I_{AC}$ that is suitable for assessing the AC corrosion risk cannot be acquired.

An object of the present invention is to address such a problem. That is, the objects of the present invention are to provide method and instrumentation for measuring and assessing that can be jointly used across regions where different commercial frequencies are employed in method and instrumentation for measuring and assessing the AC corrosion risk of pipelines, to acquire an accurate coupon AC current density that is suitable for assessing the AC corrosion risk for each region where a different commercial frequencies are employed by using a single measuring and assessing instrumentation, and to acquire an accurate coupon AC current density that is suitable for assessing the AC corrosion risk even when the source of AC corrosion cannot be clearly specified or mixed effects are brought by the source of AC corrosion that used different commercial frequencies at the measuring point for the coupon current density.

Means for Solving the Problem

To achieve such a purpose, the present invention regarding method and instrumentation for measuring and assessing the AC corrosion risk of pipelines includes at least the following configuration:

A measuring and assessing method for the AC corrosion risk of pipelines wherein the coupon is connected to the metallic pipeline buried in the earth and the AC corrosion risk of a pipeline is assessed on the basis of coupon DC current density and coupon AC current density that are acquired from the measured value of the coupon current, wherein the measuring and assessing method comprises: a step of specifying frequency to specify a frequency of a source of AC corrosion from a waveform of the measured value of the coupon current; and a step of calculating coupon current density whereby a pair of coupon DC current density and coupon AC current density is acquired from the measured value of the coupon current in one time unit by defining one cycle of the specified frequency as one time unit, and the step of specifying frequency includes: sequentially selecting a frequency from among commercial frequencies of 16⅔ Hz, 50 Hz and 60 Hz; extracting a waveform of the measured value of the coupon current with one cycle of the selected frequency; judging whether or not a difference in appearance time between a maximum value and a minimum value in the extracted waveform is equal to ½ of one cycle of the selected frequency; and specifying the selected frequency as the frequency of the source of AC corrosion when a result of the judging matches.

A measuring and assessing instrumentation of the AC corrosion risk of pipelines, wherein the coupon is connected to the metallic pipeline buried in the earth and the AC corrosion risk of a pipeline is assessed on the basis of coupon DC current density and coupon AC current density that are acquired from the measured value of the coupon current, wherein the measuring and assessing instrumentation comprises: an instrument of specifying frequency to specify a frequency of a source of AC corrosion from a waveform of the measured value of the coupon current; and an instrument of calculating coupon current density whereby a pair of coupon DC current density and coupon AC current density is acquired from the measured value of the coupon current in one time unit by defining one cycle of the specified frequency as one time unit, and the instrument of specifying frequency includes: sequentially selecting a frequency from among commercial frequencies of 16⅔ Hz, 50 Hz and 60 Hz; extracting a waveform of the measured value of the coupon current with one cycle of the selected frequency; judging whether or not a difference in appearance time between a maximum value and a minimum value in the extracted waveform is equal to ½ of one cycle of the selected frequency; and specifying the selected frequency as the frequency of the source of AC corrosion when a result of the judging matches.

Effect of the Invention

With the aforementioned features, the present invention provides the method and instrumentation for measuring and assessing that can be used jointly across regions where different commercial frequencies are employed. Further, it is possible to acquire accurate coupon AC current density that is suitable for assessing the AC corrosion risk for each region where different commercial frequencies are employed by using a single measuring and assessing instrumentation. Further, it is possible to acquire accurate coupon AC current density that is suitable for assessing the AC corrosion risk by specifying the frequency of the source of AC corrosion even when the source of AC corrosion cannot be clearly specified or mixed effects are brought by the source of AC corrosion that used different commercial frequencies at the measuring point for the coupon current density.

EMBODIMENT FOR PRACTICING THE INVENTION

Hereinafter, an embodiment of the present invention is described with reference to the drawings. FIG. 2 is a view illustrating a measuring and assessing method (flowchart) of the AC corrosion risk of a pipeline according to an embodiment of the present invention. An measuring and assessing method according to an embodiment of the present invention comprises connecting the coupon C to a metallic pipeline P that is buried in the earth in the same manner as the method shown in FIG. 1 and assessing the AC corrosion risk of a pipeline on the basis of-coupon AC current density acquired from the measured value of a coupon current. The method has a step of specifying frequency, which specifies a frequency of the source of AC corrosion from the waveform of measured value of the coupon current and a step of calculating coupon current density, which calculates single coupon AC current density from the waveform of measured value of the coupon current within one time unit by defining one cycle of the specified frequency as one time unit.

The step of specifying frequency is a step for specifying a frequency of the source of AC corrosion that generates an induced AC voltage at the pipeline P. By having the step, regardless whether or not the frequency of the source of AC corrosion is predictable, a frequency of the source of AC corrosion can be specified from the waveform of the measured value of coupon current.

Specifically, at first, coupon current I(t) is measured during a sampling interval set for a prescribed time (STEP 1). Where, the sampling interval is preferably small (for example, 0.1 ms) enough to clearly determine a change between 16⅔ Hz, 50 Hz and 60 Hz that are commercial frequencies. The measured coupon currents I(t) are stored in a store measure as time-series data corresponding to appearance times.

Next, a single frequency Fb is sequentially selected from among 16⅔ Hz, 50 Hz and 60 Hz that are commercial frequencies. Then, the waveform of measured value of a coupon current I(t) is extracted during one cycle T (=1000/Fb)[ms] of the selected frequency Fb [Hz] (STEP 3), and it is determined whether or not the appearance time difference $\Delta t$ between the maximum value and the minimum value of the extracted waveform equals to ½ of one cycle T of the selected frequency Fb (STEP 5). If $\Delta t \neq (½)*T$ (STEP 5: No), the selected frequency Fb is changed to a different commercial frequency and STEP 2 to STEP 5 are performed. Thus, if $\Delta t=(½)*T$ is satisfied (STEP 5: YES), the frequency Fb selected this time is specified as a frequency of the source of AC corrosion.

Figure 3:
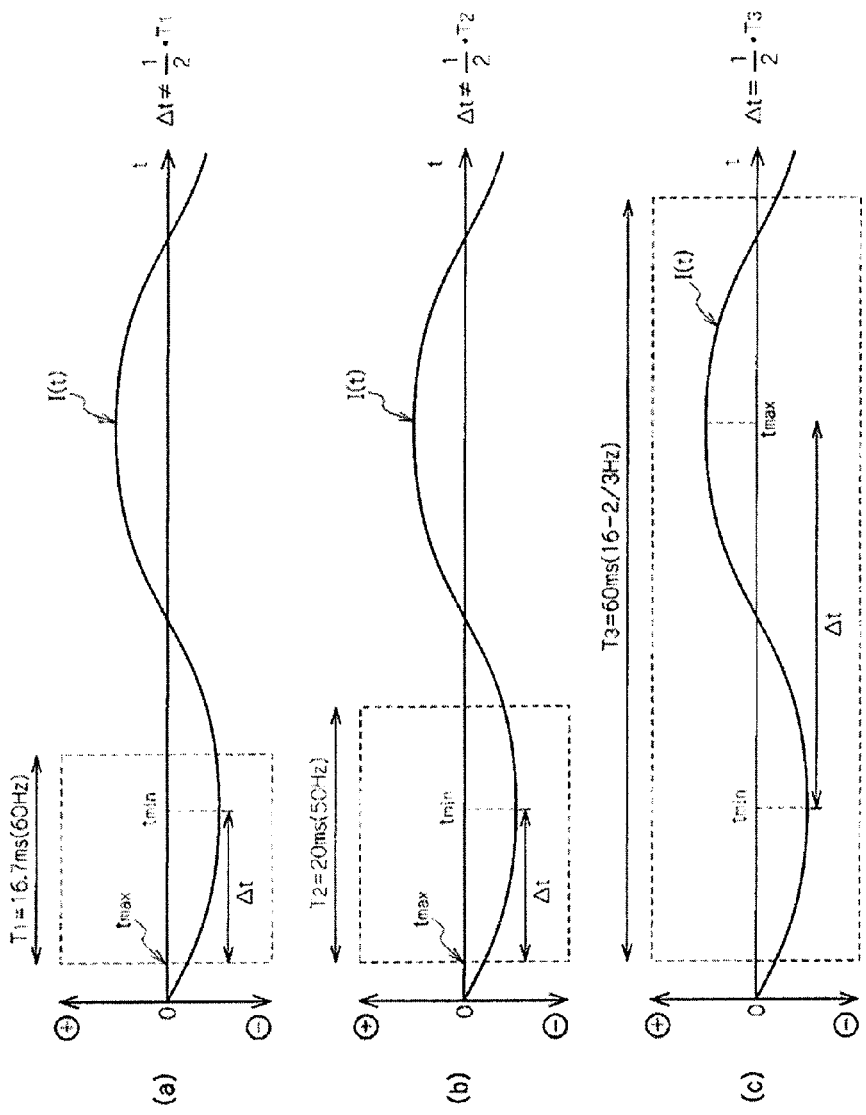
FIG. 3 is a view illustrating an example of steps to specify a frequency in an embodiment of the present invention.

FIG. 3 is a view illustrating an example of the aforementioned step of specifying the frequency. When the waveform of measured value (time-series data) of the coupon current I(t) is acquired, first, 60 Hz is selected as a frequency Fb as shown in the drawing. The one cycle T1 of 60 Hz is 16.7 ms and the waveform of measured value is extracted during the one cycle T1 so that an appearance time difference $\Delta t$ between the appearance time $t_{max}$ of the maximum value and the appearance time $t_{min}$ of the minimum value in the extracted waveform is acquired. Then, whether or not the acquired $\Delta t$ equals to $(½)*T1$ is determined. In the example shown in FIG. 3(a), the equation $\Delta t \neq (½)*T1$ is satisfied, and thus 50 Hz is subsequently selected as the frequency Fb. The one cycle T2 of 50 Hz is 20 ms and the waveform of measured value is extracted during the one cycle T2 so that an appearance time difference $\Delta t$ between the appearance time $t_{max}$ of the maximum value and the appearance time $t_{min}$ of the minimum value in the extracted waveform is acquired. Then, whether or not the acquired $\Delta t$ equals to $(½)*T2$ is determined. In the example shown in FIG. 3(b), the equation $\Delta t \neq (½)*T1$ is satisfied, and thus 16⅔ Hz is subsequently selected as the frequency Fb.

The one cycle T3 of 16⅔ Hz is 60 ms and the waveform of measured value is extracted during the one cycle T3 so that an appearance time difference $\Delta t$ between the appearance time $t_{max}$ of the maximum value and the appearance time $t_{min}$ of the minimum value in the extracted waveform is acquired. Then, whether or not the acquired $\Delta t$ equals to $(½)*T3$ is determined. In the example shown in FIG. 3(c), the equation $\Delta t=(½)*T1$ is satisfied, and thus a frequency of the source of AC corrosion can be specified as 16⅔ Hz from the waveform of measured value of the coupon current I(t) shown in this example.

In FIG. 2, when the frequency Fb of the source of AC corrosion is specified (STEP 6), steps to calculate coupon current density are performed, which acquires one coupon AC current density $I_{AC}$ from the waveform of measured value of the coupon current I(t) within one time unit by defining one cycle of the specified frequency as the one time unit.

Specifically, the above-mentioned one time unit is set as a subunit and a series of a plurality of the subunit is set as one unit (STEP 7). Then, the coupon DC current density $I_{DC}$ and the coupon AC current density $I_{AC}$ are acquired for each of the subunit (STEP 8). Before acquiring the coupon AC current density $I_{AC}$, the coupon DC current density $I_{DC}$ is necessarily acquired.

After that, the coupon DC current density $I_{DC}$ and the coupon AC current density $I_{AC}$ acquired for each subunit are compared within one unit and the average values $I_{DC}^{ave}$ and $I_{AC}^{ave}$, the maximum values $I_{AC}^{max}$ and $I_{AC}^{max}$, and the minimum values $I_{DC}^{min}$ and $I_{AC}^{min}$ are acquired (STEP 9).

Thus, on the basis of these values ($I_{DC}^{ave}$, $I_{DC}^{max}$, $I_{DC}^{min}$, $I_{AC}^{ave}$, $I_{AC}^{max}$ and $I_{AC}^{min}$), the AC corrosion risk of a pipeline is assessed (STEP 10).

Figure 4:
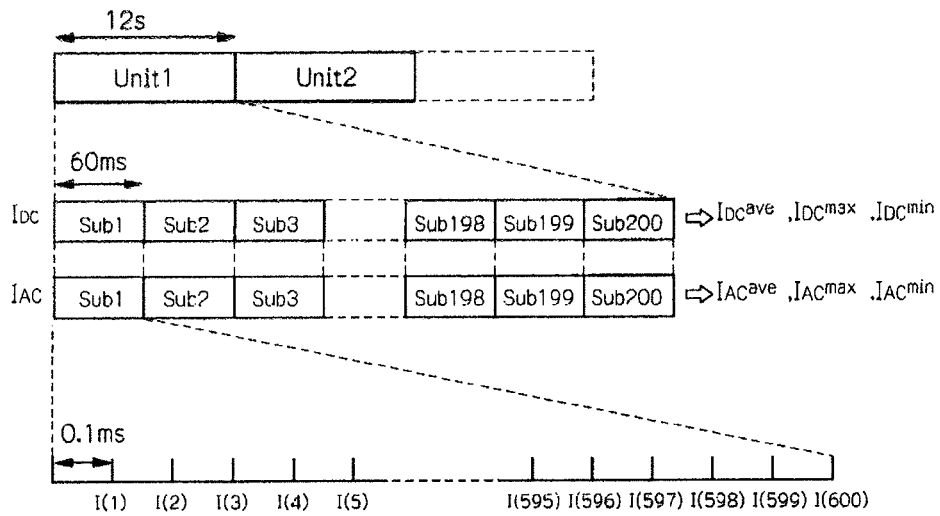
FIG. 4 is a view illustrating an example of steps to calculate coupon current density in an embodiment of the present invention.
Figure 4:
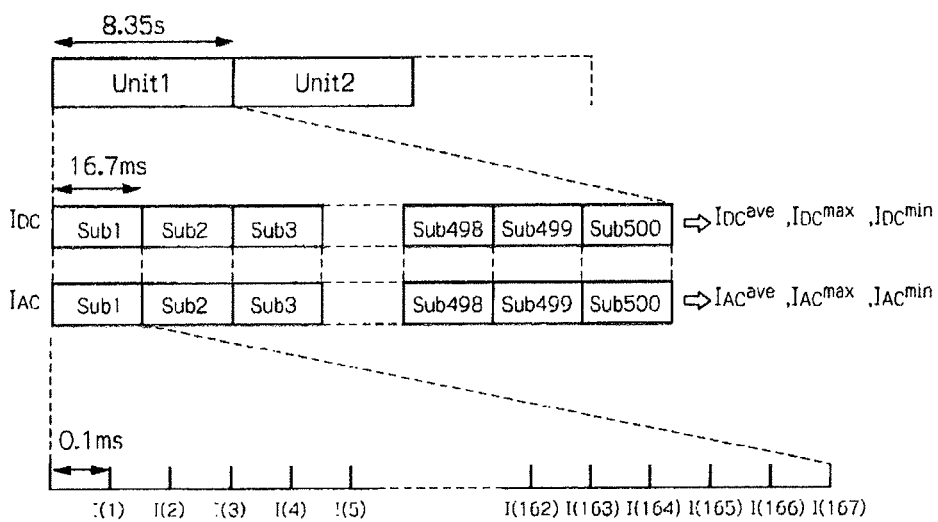

FIG. 4 is a view illustrating an example of steps to calculate coupon current density. The one subunit and the one unit in each frequency Fb after the frequency Fb is specified can be set as shown in a below mentioned table 1.

TABLE 1

| | One subunit | One unit | |
|---|---|---|---|
| Frequency (Hz) | Measuring time (ms) | A total number of subunit | Measuring time (s) |
| 16-2/3 | 60 | 200 | 12 |
| 50 | 20 | 500 | 10 |
| 60 | 16.7 | 500 | 8.35 |

The measuring time for one unit must be set to allow the AC corrosion risk caused on the pipeline P by a high-speed train passing on a railway track to be sufficiently determined.

The high-speed train means a train that runs at a speed of 200 km per hour or more in a major section and a route therefore, which is the same definition as that of the Shinkansen in Japan. If the length of a car of the high-speed train is 25 m and the train consists of 16 cars, then the length of one train is 400 m. It takes 7.2 seconds for a high-speed train to pass through a measuring point for coupon current density at a speed of 200 km per hour. As such, if the measuring time for one unit is set in the range of 8.35-12 s, the AC corrosion risk caused on the pipeline by a high-speed train passing therethrough can be sufficiently determined regardless of frequency.

FIG. 4($a$) shows an calculation example of coupon current density when the frequency Fb is specified as 16⅔ Hz. In this case, the measuring time for one subunit is set to be 60 ms and the measuring time for one unit is set to be 12 s and the coupon DC current density $I_{DC}$ and the coupon AC current density $I_{AC}$ are acquired by the following equation (3) and (4).

$$I_{DC} = \frac{1}{A} \frac{1}{600} \sum_{t=1}^{600} I(t) \qquad (3)$$

$$I_{AC} = \frac{1}{A} \sqrt{\frac{1}{600} \sum_{t=1}^{600} \{I(t) - I_{DC}\}^2} \qquad (4)$$

FIG. 4($b$) shows an example of calculating coupon current density when frequency Fb is specified as 60 Hz. In this case, the measuring time for one subunit is set to be 16.7 ms and the measuring time for one unit is set to be 8.35 s and the coupon DC current density $I_{DC}$ and the coupon AC current density $I_{AC}$ are acquired by the following equations (5) and (6).

$$I_{DC} = \frac{1}{A} \frac{1}{167} \sum_{t=1}^{167} I(t) \qquad (5)$$

$$I_{AC} = \frac{1}{A} \sqrt{\frac{1}{167} \sum_{t=1}^{167} \{I(t) - I_{DC}\}^2} \qquad (6)$$

Figure 1:
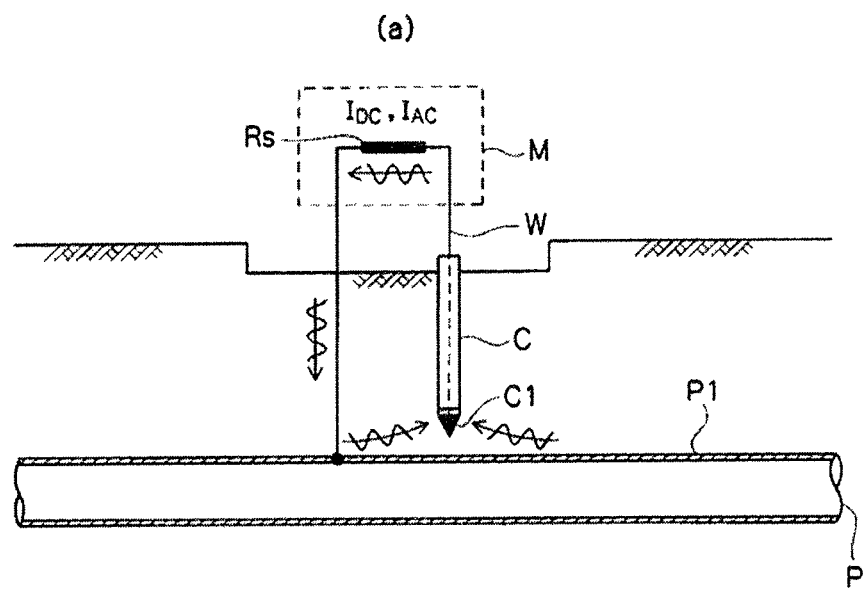
FIG. 1 is a view illustrating a method for measuring coupon current density on a pipeline.
Figure 1:
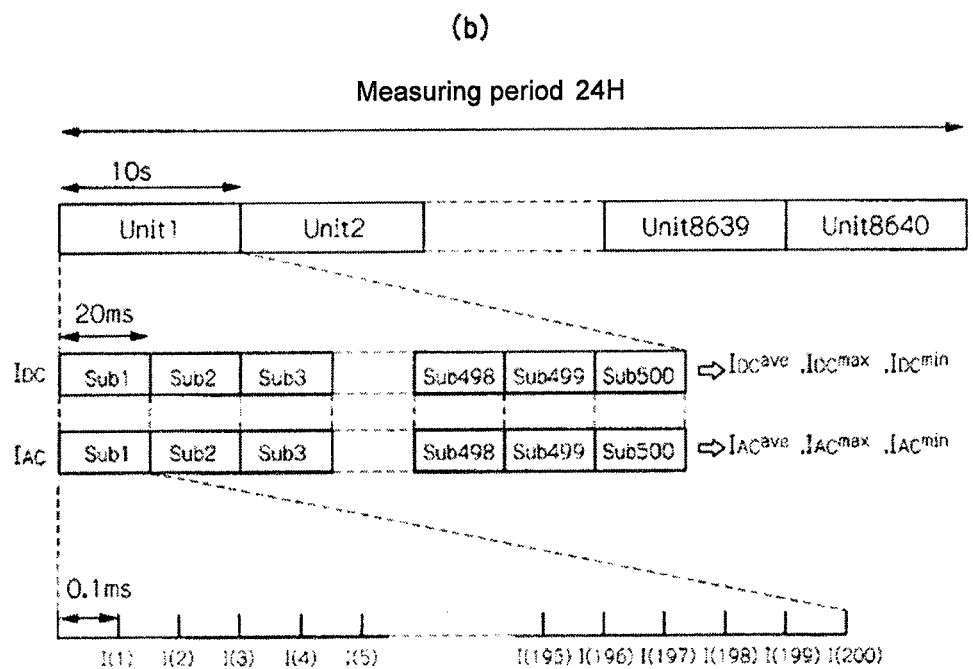
Figure 2:
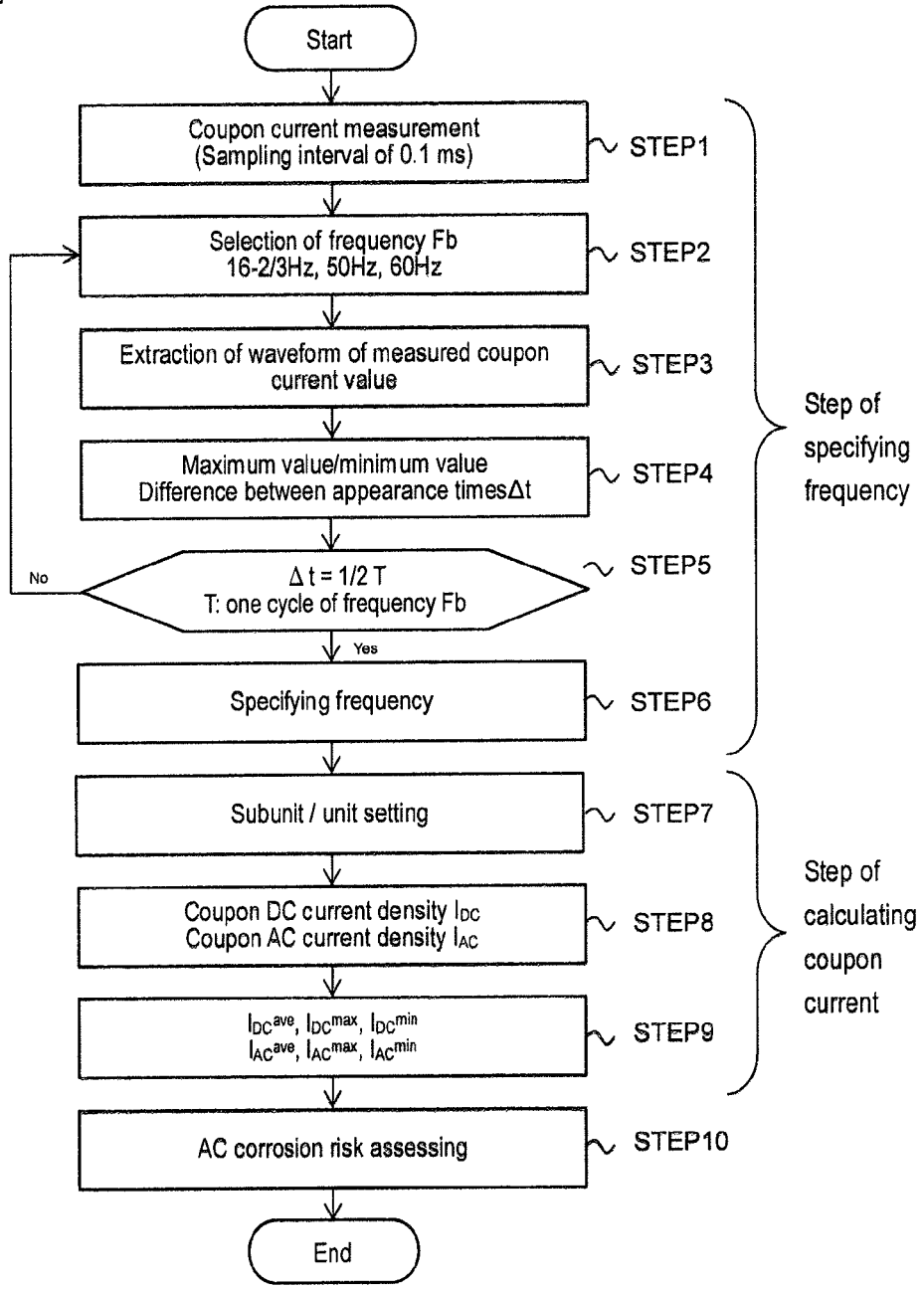
FIG. 2 is a view illustrating a measuring and assessing method (flowchart) for the AC corrosion risk of a pipeline according to an embodiment of the present invention.

An example of calculating the coupon current density when frequency Fb is specified as 50 Hz is shown in FIG. 1($b$) and the equations for calculation are the same as the aforementioned equations (1) and (2).

Figure 5:
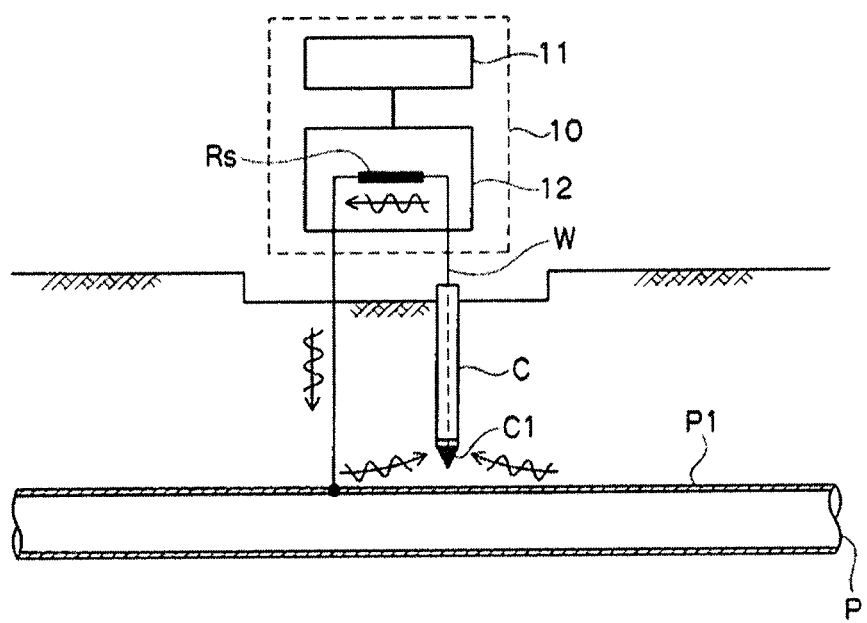
FIG. 5 is a view illustrating measuring and assessing instrumentation of the AC corrosion risk of a pipeline according to an embodiment of the present invention.

FIG. 5 is a view illustrating instrumentation for measuring and assessing of the AC corrosion risk of a pipeline according to an embodiment of the present invention. Instrumentation for measuring and assessing 10 is a device constituted by connecting the coupon C with a metallic pipeline P buried in the earth to assess the AC corrosion risk of the pipeline P on the basis of coupon DC current density and coupon AC current density that are acquired from the measured value of a coupon current, and the device is provided with an apparatus of specifying the frequency 11 and an instrument of calculating coupon current density 12.

The apparatus of specifying the frequency 11 can be constituted by a control device such as a portable PC and a programmable controller, and is provided with a program to perform the aforementioned steps to specify the frequency on the basis of the waveform of measured value of a coupon current (t) that is acquired from the instrument of calculating coupon current density 12. Frequency specified by the apparatus of specifying the frequency 11 is output to the instrument of calculating coupon current density 12.

The instrument of calculating coupon current density 12 is provided with a program to perform the above-described steps to calculate coupon current density. The measuring times for one subunit and one unit are set from the frequency specified by the apparatus of specifying the frequency 11. Coupon DC current density $I_{DC}$ and coupon AC current density $I_{AC}$ are calculated from the coupon current I(t) measured at the sampling interval of 0.1 ms and the $I_{DC}^{ave}$, $I_{DC}^{max}$, $I_{DC}^{min}$, $I_{AC}^{ave}$, $I_{AC}^{max}$, and $I_{AC}^{min}$ are acquired for each unit.

According to the method for measuring and assessing of the AC corrosion risk of pipelines or the instrumentation for measuring and assessing 10 for performing the method, which have the above-described features, the frequency of the source of AC corrosion can be specified by the measured coupon current I(t), and thus the measuring times for one subunit and one unit are set each time on the basis of the specified frequency. Thereby, accurate coupon DC current density $I_{DC}$ and coupon AC current density $I_{AC}$ as an index of assessing the AC corrosion risk can be acquired.

As such, wherever measuring and assessing of the AC corrosion risk are performed, the coupon DC current density $I_{DC}$ and the coupon AC current density $I_{AC}$ that are indexes for assessing the AC corrosion risk can be accurately acquired regardless of the difference in the commercial frequency for each region. Further, even when the source of AC corrosion is not clearly specified or mixed effects are brought by the source of AC corrosion that used different commercial frequencies at the measuring point for the coupon current density, since the frequency of the source of AC corrosion can be specified when performing the measuring and assessing, the accurate values of coupon DC current density $I_{DC}$ and coupon AC current density $I_{AC}$ can be acquired on the basis of the specified frequency.

DESCRIPTION OF THE SYMBOLS

10: instrumentation for measuring and assessing,
11: apparatus of specifying a frequency, 12: instrument of calculating coupon current density,
P: pipeline, P1: coating, C: coupon, W: wire
Rs: shunt resistor, M: measuring instrumentation

The invention claimed is:
1. A measuring and assessing method for an AC corrosion risk of a pipeline, wherein a coupon is connected to a metallic pipeline buried in earth, and the AC corrosion risk of the pipeline is assessed based on a coupon DC current density and a coupon AC current density that are acquired from a measured value of a coupon current, the measuring and assessing method comprising:
specifying a frequency of a source of AC corrosion from the measured value of the coupon current; and
calculating a coupon current density by acquiring a pair of the coupon DC current density and the coupon AC current density from the measured value of the coupon current in one time unit by defining one cycle of the specified frequency as the one time unit,
wherein the specifying of the frequency includes:
sequentially selecting a candidate frequency from among commercial frequencies of 16⅔ Hz, 50 Hz and 60 Hz;
extracting a waveform of the measured value of the coupon current with one cycle of the selected candidate frequency;
judging whether or not a difference in appearance time between a maximum value and a minimum value in the extracted waveform is equal to ½ of the one cycle of the selected candidate frequency; and
specifying the selected candidate frequency as the frequency of the source of AC corrosion when a result of the judging is equal.

2. The measuring and assessing method for the AC corrosion risk of the pipeline according to claim 1, wherein the measuring and assessing method further comprises:
setting the one time unit as a subunit and setting a series of a plurality of the subunit as one unit;
acquiring a maximum value and a minimum value in the one unit by comparing the coupon DC current density with the coupon AC current density that are acquired for each subunit; and
assessing the AC corrosion risk of the pipeline based on the maximum value and the minimum value.

3. The measuring and assessing method for the AC corrosion risk of the pipeline according to claim 2, wherein a measuring time for the one unit is set to be 12 s when the frequency of the source of AC corrosion is specified as 16⅔ Hz, is set to be 10 s when the frequency of the source of AC corrosion is specified as 50 Hz, and is set to be 8.35 s when the frequency of the source of AC corrosion is specified as 60 Hz.

4. The measuring and assessing method for the AC corrosion risk of the pipeline according to claim 1, wherein the waveform of the measured value of the coupon current includes time-series data of the coupon current that is measured at a sampling interval of 0.1 ms.

5. A measuring and assessing instrumentation of an AC corrosion risk of a pipeline, wherein a coupon is connected to a metallic pipeline buried in earth, and the AC corrosion risk of the pipeline is assessed based on a coupon DC current density and a coupon AC current density that are acquired from a measured value of a coupon current, the measuring and assessing instrumentation comprising:
an instrument of specifying frequency to specify a frequency of a source of AC corrosion from the measured value of the coupon current; and
an instrument of calculating a coupon current density by acquiring a pair of the coupon DC current density and the coupon AC current density from the measured value of the coupon current in one time unit by defining one cycle of the specified frequency as the one time unit,
wherein the instrument of specifying frequency performs operations including:
sequentially selecting a candidate frequency from among commercial frequencies of 16⅔ Hz, 50 Hz and 60 Hz;
extracting a waveform of the measured value of the coupon current with one cycle of the selected candidate frequency;
judging whether or not a difference in appearance time between a maximum value and a minimum value in the extracted waveform is equal to ½ of the one cycle of the selected candidate frequency; and
specifying the selected candidate frequency as the frequency of the source of AC corrosion when a result of the judging is equal.

6. The measuring and assessing method for the AC corrosion risk of the pipeline according to claim 2, wherein the waveform of the measured value of the coupon current includes time-series data of the coupon current that is measured at a sampling interval of 0.1 ms.

7. The measuring and assessing method for the AC corrosion risk of the pipeline according to claim 3, wherein the waveform of the measured value of the coupon current includes time-series data of the coupon current that is measured at a sampling interval of 0.1 ms.

8. The measuring and assessing method for the AC corrosion risk of the pipeline according to claim 1, wherein the specifying of the frequency is configured to specify the selected candidate frequency as the frequency of the source of AC corrosion without selecting each of the commercial frequencies when the result of the judging is equal before each of the commercial frequencies is selected.

9. The measuring and assessing method for the AC corrosion risk of the pipeline according to claim 2, wherein a measuring time for the one unit is different for each of the commercial frequencies, from which the frequency of the source of AC corrosion is specified.

10. A system for measuring and assessing an AC corrosion risk of a pipeline, the system comprising:
a coupon connected to a metallic pipeline buried in earth, the AC corrosion risk of the pipeline being assessed based on a coupon DC current density and a coupon AC current density that are acquired from a measured value of a coupon current; and
a computer including a program that, when executed by the computer, causes the computer to perform operations including:
specifying a frequency of a source of AC corrosion from the measured value of the coupon current; and
calculating a coupon current density by acquiring a pair of the coupon DC current density and the coupon AC current density from the measured value of the coupon current in one time unit by defining one cycle of the specified frequency as the one time unit,
wherein the specifying of the frequency includes:
sequentially selecting a candidate frequency from among a plurality of commercial frequencies;
extracting a waveform of the measured value of the coupon current with one cycle of the selected candidate frequency;
judging whether or not a difference in appearance time between a maximum value and a minimum value in the extracted waveform is equal to ½ of the one cycle of the selected candidate frequency; and
specifying the selected candidate frequency as the frequency of the source of AC corrosion when a result of the judging is equal.

11. The system according to claim 10, further comprising:
a wire electrically interconnecting the coupon and the metallic pipeline; and
a shunt resistor provided in the wire which electrically connects the coupon with the pipeline,
wherein the computer measures the coupon current flowing through the shunt resistor.

\* \* \* \* \*